United States Patent [19]

Breidegam

[11] Patent Number: 4,577,256
[45] Date of Patent: Mar. 18, 1986

[54] WOVEN STRETCHABLE GROUNDING STRAP

[75] Inventor: Albert C. Breidegam, Sharpsburg, Ga.

[73] Assignee: Semtronics Corporation, Peachtree City, Ga.

[21] Appl. No.: 654,636

[22] Filed: Sep. 25, 1984

[51] Int. Cl.[4] ............................................. H05F 3/02
[52] U.S. Cl. .................................... 361/220; 57/901; 361/212
[58] Field of Search ....................... 361/212, 220, 223; 57/901

[56] References Cited

U.S. PATENT DOCUMENTS

| | | |
|---|---|---|
| 1,531,862 | 3/1925 | Larned . |
| 3,063,447 | 11/1962 | Kirsten ............................. 361/220 X |
| 3,377,509 | 4/1968 | Legge . |
| 3,422,460 | 1/1969 | Burke et al. ............................... 2/73 |
| 3,424,698 | 1/1969 | Lupinski et al. ..................... 252/500 |
| 3,459,997 | 8/1969 | Legge . |
| 3,541,389 | 11/1970 | Van Name . |
| 3,582,448 | 6/1971 | Okuhashi .............................. 161/87 |
| 3,596,134 | 7/1971 | Burke . |
| 3,699,590 | 10/1972 | Webber et al. .................. 361/220 X |
| 3,812,861 | 5/1974 | Peters .................................... 128/418 |
| 3,832,841 | 9/1974 | Cole ..................................... 57/152 |
| 3,851,456 | 12/1974 | Hamada et al. ....................... 57/140 |
| 3,857,397 | 12/1974 | Brosseau .............................. 128/384 |
| 3,904,929 | 9/1975 | Kanaya et al. . |
| 3,949,129 | 4/1976 | Hubbard .............................. 428/190 |
| 3,986,530 | 10/1976 | Maekawa .............................. 139/425 |
| 3,987,613 | 10/1976 | Woods et al. ......................... 57/140 |
| 4,267,233 | 5/1981 | Tanaka et al. ....................... 428/389 |
| 4,321,789 | 3/1982 | Dammann et al. ................... 57/224 |
| 4,373,175 | 2/1983 | Mykkanen ........................... 361/220 |
| 4,398,277 | 8/1983 | Christiansen et al. .............. 361/220 |
| 4,402,560 | 9/1983 | Swainbank ............................. 339/11 |
| 4,420,529 | 12/1983 | Westhead ............................. 139/244 |
| 4,422,483 | 12/1983 | Zins ..................................... 139/420 |
| 4,475,141 | 10/1984 | Antonevick .................... 361/212 X |

FOREIGN PATENT DOCUMENTS 2547390 5/1977 Fed. Rep. of Germany .
1067260 8/1965 United Kingdom .

Primary Examiner—Harry E. Moose, Jr.
Attorney, Agent, or Firm—Kilpatrick & Cody

[57] ABSTRACT

A woven strap that may be comfortably worn on the wrist to drain or wick static electrical charges from the wearer. Conductive fibers on the inside surface of the strap contact the skin and conduct electrical charges to a grounding cord attached to the strap. Face yarns exposed on the outer surface may be woven to form designs. The woven fabric material of the strap is attached to a clasp allowing the strap to be adjustable in size. Because of the woven nature of the fabric material and the adjustable clasp, the strap is more comfortable than other conductive elastic wrist straps. The woven fabric material is particularly advantageous because it stretches easily, it is inexpensive, and it does not roll over onto itself as it is being drawn over the hand.

17 Claims, 13 Drawing Figures

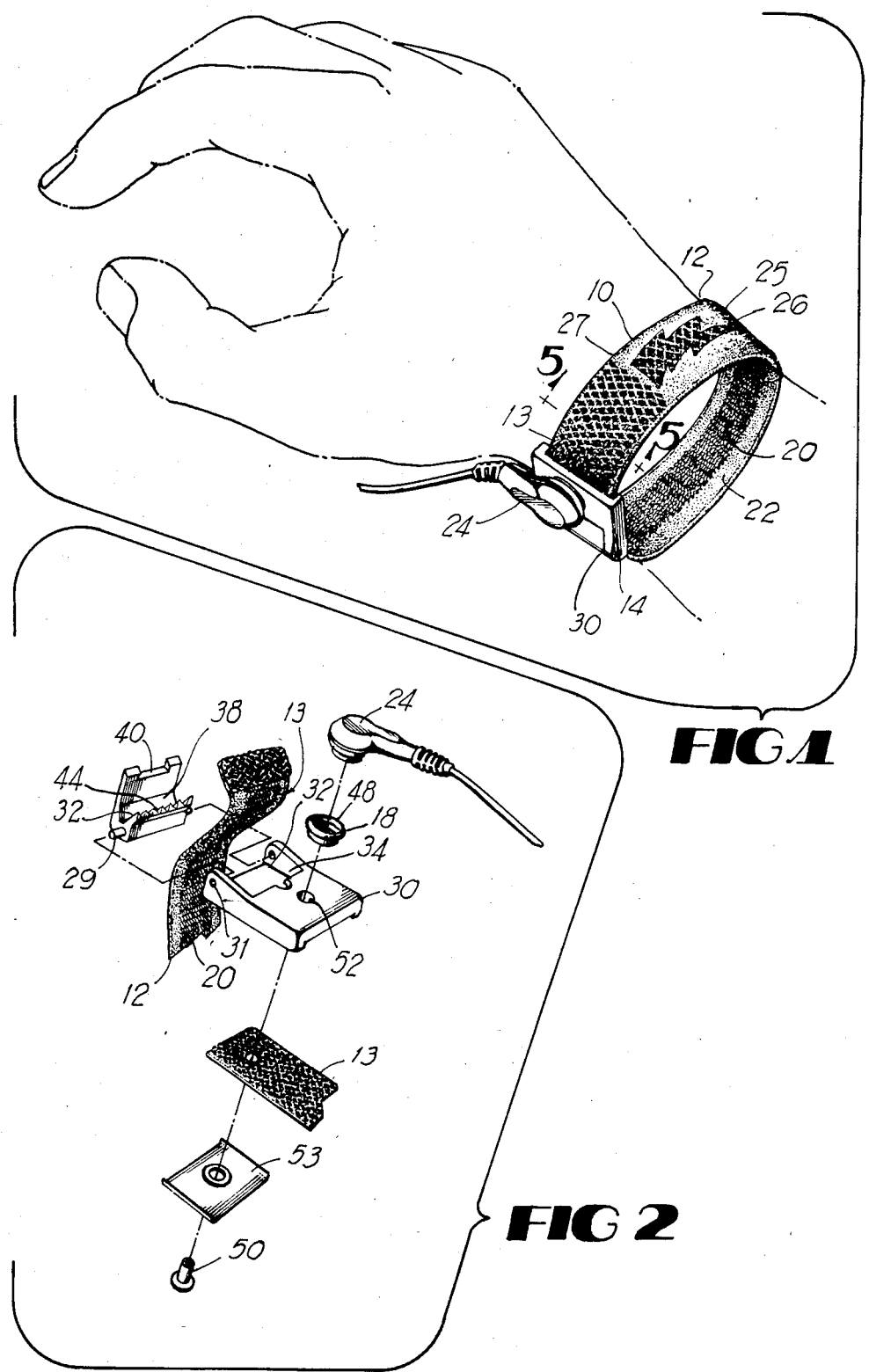

WOVEN STRETCHABLE GROUNDING STRAP

BACKGROUND OF THE INVENTION

This invention pertains to a woven strap that may be comfortably worn on the leg or arm to drain or wick static electrical charges from the wearer.

Static electricity provides problems in the electronics and other industries, particularly with the advent of integrated circuits and other microelectronic components. Components such as integrated circuits, for instance, may be disabled or destroyed by over-voltages or power density resulting from static electricity. Certain junctions in such circuits can be destroyed by as little as a 50-volt potential, which radically changes the doping structure in their lattices. Power densities resulting from excessive potential and imperfections in circuit layout or structure can vaporize or radically alter the silicon substrate and thus impair or destroy a circuit's performance. Yet a person walking on a carpet on a dry day can accumulate as much as 30,000 volts of potential, and he can triboelectrically generate thousands of volts by simply changing his position in his chair or handling a styrofoam cup.

Such person can inadvertently discharge such static electric potential into the circuit or component by touching it and causing overvoltage or exessive power density. Additionally, the potential in such a person's body can induce a charge in a circuit that can later cause overvoltage or excessive power density when the circuit is subsequently grounded.

More and more frequently, therefore, those in industries in which integrated circuits and other microelectronic components are handled or assembled are taking measures to limit the failure rate of those circuits and components by attempting to keep them as well as their environment at zero electrical potential. Such measures include providing workers and work stations with anti-static carpet, conductive or dissipative grounded desk top work surfaces, hot air ion generators which emit ions to neutralize static charges, and grounding straps to keep workers at zero potential. The term "conductive" herein, and according to its customary usage in the art, means an electrical resistance of between zero and $10^5$ ohms. Similarly, "dissipative" means a resistance of between $10^5$ and $10^9$ ohms, "anti-static" means a resistance of between $10^9$ and $10^{14}$ ohms, and "insulative" means a resistance of more than $10^{14}$ ohms.

A grounding strap must have several features in order to perform its grounding function effectively. First, it must ensure that the wearer's skin is electrically connected to ground. This connection is typically accomplished by a conductive surface on the inside of the strap contacting the skin. The conductive surface is electrically connected to a grounding cord which leads from the strap to a grounded electrical connection. If the electrical contacting means on the inside of the strap becomes dirty or fouled by oil, perspiration or hair, the strap may lose its effectiveness. It is therefore important to use a conductive material on the inner surface of the strap that does not easily become dirty or fouled.

Second, comfort is a premium consideration, because if the strap is uncomfortable, the wearer will be tempted to remove it and can thereby cause damage to electrical components on which he is working. A strap that is easily stretchable, that breathes, that is attractive and that poses mimimum inconvenience to the wearer is therefore highly desired.

The situations in which grounding wrist straps are used heightens the importance of their being comfortable so that they are continuously worn and maintain continuous electrical contact with the skin. A person working on microelectronic components or integrated circuits may be completely unaware that he has accumulated minor static electrical charges, and may therefore unknowingly be in a position to disable circuits on which he is working or which he is handling. If his strap is loose or he has removed it, he may be unaware that electrical discharges transmitted from his fingers are disabling these circuits. (A typical person cannot sense a static electrical discharge of less than approximately 3,500 volts.) No one may discover that the circuits have been disabled or damaged until hours, days or weeks later, when the circuits have been placed in components or devices which fail in the field. Removal and repair or replacement of these circuits once in the field is far costlier than avoiding potential failure while the wearer is handling the circuits. Thus, the wearer's employer typically must depend upon the effectiveness of the wrist strap to maintain a lower failure rate of such electronic circuits and components, by maintaining continuous electrical contact with the wearer's wrist and by providing him minimum temptation to remove the strap from his wrist.

These considerations have been addressed by several types of grounding straps. U.S. Pat. No. 4,373,175 issued Feb. 8, 1983 to Mykkanen ("Mykkanen"), for instance, discloses an extensible metal band similar to a Speidel watch band on which a snap fastener for a grounding cord is attached. Such a strap can be uncomfortable, however, and its conductive metal outer surface can prove dangerous to the wearer if it contacts an electrical potential sufficient to electrocute the wearer.

A more comfortable grounding strap is disclosed in U.S. Pat. No. 3,857,397 issued Dec. 31, 1974 to Brosseau ("Brosseau"). Outer and inner conductive polyolefin layers sandwich an intermediate nylon scrim layer to form the band. Hook and loop (Velcro ®) fastening material holds the strap on the wrist. This strap is typical of a number of straps having carbon-suffused synthetics or other conductive polyolefins. Body oil and minerals can accumulate on such surfaces and interfere with electrical contact between the band and the skin. Further, carbon particles tend to wear off onto the wrist, causing black stripes on the wrist. The non-stretchable nature of such bands means that the wearer must adjust them to be tight enough to cause sufficient electrical contact, but loose enough to be comfortable, and skin contact can be lost or intermittent.

Another approach to many of these problems is disclosed in U.S. Pat. No. 4,398,277 issued Aug. 9, 1983 to Christiansen and Westberg ("Christiansen"). This strap is made of knitted stretchable fabric containing stainless steel fibers. A plastic and metal fitting permanently closes the strap into a loop of predetermined size and has a connection for a grounding cord. This strap can prove uncomfortable to the wearer, however, unless his wrist comports with the predetermined strap size offered by the manufacturer. Further, the knitted fabric permits the strap to roll over on itself as it is being pulled over the hand and causes the strap to become thinner as it is stretched. Because the fabric is knitted, it can also "pull" and "run" when snagged. Perhaps more important, it has been discovered that the electrical conductivity of the Christiansen strap decreases as the strap is relaxed, and thus varies from one stretched state to another. This phenomenon probably occurs because the metallic strands in the conductive yarns are pulled more tightly together in the knitted material as it is stretched and are separated from one another to a certain extent in the knitted conductive yarns as the strap is relaxed.

SUMMARY OF THE INVENTION

The strap of this invention utilizes woven material and has a clasp allowing its size to be adjusted. The woven fabric has longitudinally oriented electrically conductive fibers on its inner surface. Face yarns on its outer surface may form letters, words, logos or other pleasing or commercially attractive designs. Elastic yarns allow the material to stretch more easily and therefore more comfortably than knitted material. Because weaving is in general a less expensive process than knitting and because the elastic and conductive fibers run only in one direction, longitudinally, rather than running in, around and through the large numbers of loops of knitted fabric, the woven material of this strap is significantly less expensive than knitted fabrics. The adjustable clasp avoids the need to manufacture two or more models of the strap for different sized wrists and makes the strap markedly more comfortable for all sizes of wrists. This reduces the wearer's temptation to remove the strap and thus reduces the chance circuits and components will be damaged by the wearer's static charges. Further, the clasp is preferably made of anti-static rather than insulative material in order to avoid inadvertent generation or accumulation of static electricity on the clasp that could later cause harm to circuits or components.

It is therefore an object of this invention to provide an inexpensive woven stretchable grounding strap that is comfortable and adjustable in size, so that wearers will be less tempted to remove it or impair its effectiveness, than in using previous straps.

It is another object of this invention to provide a woven stretchable grounding strap the conductivity of which varies insignificantly between its relaxed state and its stretched state.

It is another object of this invention to provide a woven stretchable grounding strap on the outer surface of which may be woven letters, words, logos or other attractive designs.

It is another object of this invention to provide a woven stretchable grounding strap that is not conductive on its outer surface.

It is a further object of this invention to provide a woven stretchable grounding strap that does not become narrower when stretched, that stretches more easily than knitted fabrics and that does not roll over onto itself as it is being drawn over the hand.

Other objects, features and advantages of this invention will be apparent in the specification, claims and drawings herein.

BRIEF DESCRIPTION OF THE DRAWINGS

FIG. 1 is a perspective view of a preferred embodiment of a woven stretchable grounding strap of this invention.

FIG. 2 is an exploded perspective view of the clasp of the strap of FIG. 1.

DETAILED DESCRIPTION OF THE DRAWINGS

Figure 3:
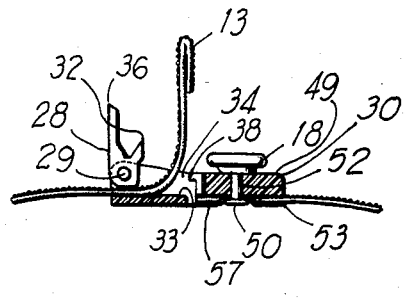
FIG. 3 is a cross sectional view of the clasp of FIG. 2, in the open position.

FIG. 1 illustrates a preferred embodiment of the strap 10 of this invention. Woven material 12 of the strap 10 is connected to a clasp 14. A fastener 18 mounted on clasp 14 and electrically connected to conductive yarns 20 on the inner surface 22 of material 12 receives a grounding cord 24. Grounding cord 24, which may contain a 1 megohm resistor to prevent electric shock if grounding cord 24 contacts a power source, carries body electrostatic charges from the wearer's wrist to electrical ground. Face yarns 25 on the outer surface 27 of material 12 impart a design 26 on outer surface 27. Design 26 improves the appearance and marketability of strap 10. Face yarns 25 may be of various colors and may form designs 26 including letters, words, logos, or other aesthetically pleasing or commercially desirable configurations.

Figure 4:
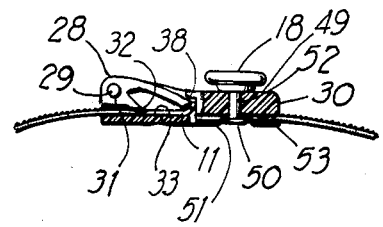
FIG. 4 is an exploded perspective view of the clasp of FIG. 2, in the closed position.

FIGS. 2-4 show more clearly the clasp 14 of the strap 10 of FIG. 1. A gate 28 is pivotally mounted in a clasp body 30 by pins 29 and pinholes 31 to capture material 12 when desired. Jam 32 on gate 28 forces second end 11 of material 12 against the bottom 33 of recess 34 of body 30 when gate 28 is closed into position. Edge 36 of gate 28 is biased against and cooperates with lip 38 of body 30 to hold gate 28 shut. Edge 36 may have a recess 40 to make it easier to snap gate 28 shut, and jam 32 may have teeth 44 to allow it to grip more tightly second end 11 of material 12.

Clasp body 30 and gate 28 should be made of antistatic material to minimize risk of inadvertent electrical contact of a conductive clasp 14 with an electrical power source and subsequent electrocution of the wearer, while simultaneously avoiding unwanted generation of static electricity on the clasp that could occur if the clasp were made of insulative material. Yet they should be made of material hard enough to capture material 12 firmly and resilient enough to be sufficiently durable. In the preferred embodiment, clasp body 30 and gate 28 are of nylon, which because of its hygroscopic properties is antistatic, but other suitable polymeric materials may be used.

Clasp 14 also serves as a mounting base for grounding cord 24. In the preferred embodiment as shown in FIGS. 2-4, a free-swivel snap or faster 18 connects to grounding cord 24. Faster 18 is physically connected to the outer, first surface 49 of clasp body 30 by rivet 50 passing through opening 52 in clasp body 30. Metallic plate 53 and first end 13 of woven material 12 are also connected to the interior surface of body 30 by rivet 50, which passes through holes in each of them. Metallic plate 53 may be of any suitable corrosion resistant metal, and serves as an additional electrical contact with the wearer's wrist, as well as holding material 12 against the inner, second surface 51 of clasp body 30. In the preferred embodiment, plate 53 is of stainless steel.

Figure 7:
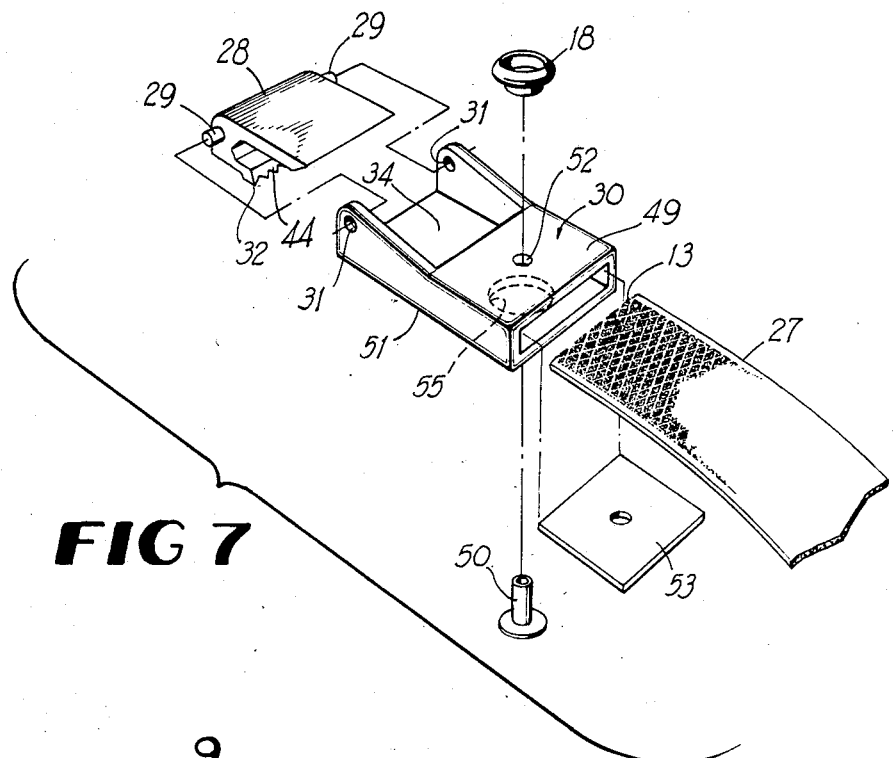
FIG. 7 is a perspective view of a second embodiment of a clasp of this invention.
Figure 8:
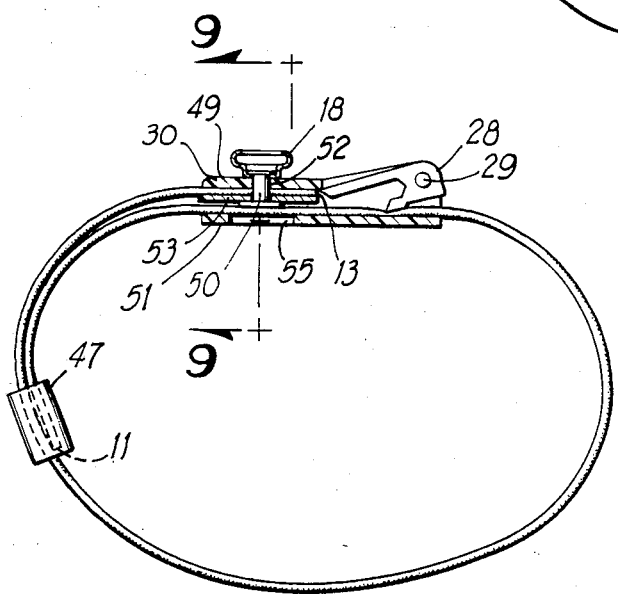
FIG. 8 is a side cross-sectional view of the clasp of FIG. 7.
Figure 9:
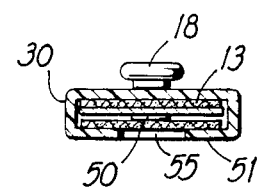
FIG. 9 is a lengthwise cross-sectional view of the clasp of FIG. 7.
Figure 10:
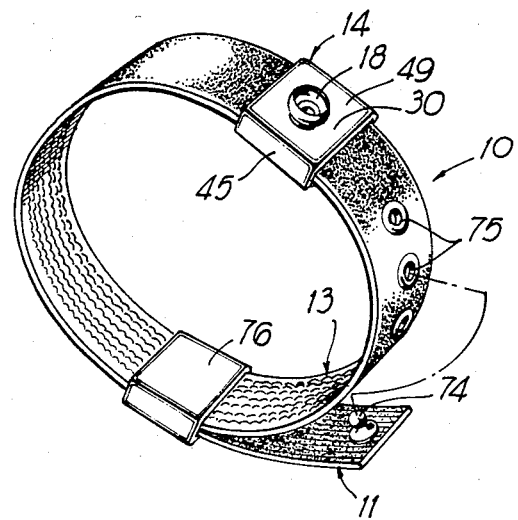
FIG. 10 is a perspective view of a third embodiment of a clasp of this invention.
Figure 11:
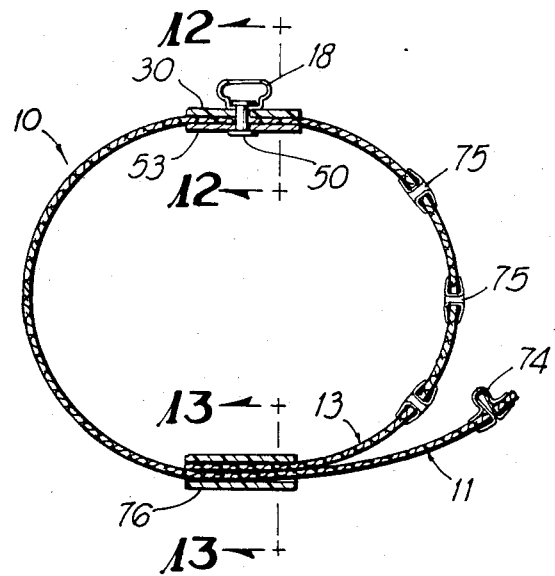
FIG. 11 is a side cross-sectional view of the clasp and strap of FIG. 10.
Figure 12:
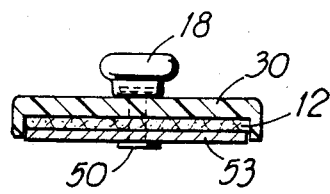
FIG. 12 is a lengthwise cross-sectional view of the clasp of FIG. 10.
Figure 13:
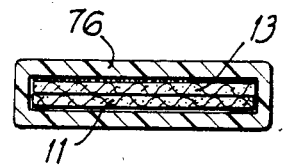
FIG. 13 is a lengthwise cross-sectional view of the retainer of FIG. 10.

In a second embodiment of clasp 14 shown in FIGS. 7, 8 and 9, clasp body 30 is essentially hollow so that two thicknesses of woven material 12 may pass through body 30 to allow strap 10 to be adjusted without the need to cut second end 11 of material 12. In this embodiment, second end 11 of material 12 is attached to a hollow loop 47 which slidably receives first end 13 of material 12 so that second end 11 of material 12 may slide along the inner surface of first end 13 of material 12 as strap 10 is adjusted. As shown in FIGS. 7, 8 and 9, the gate 28 and lip 38 mechanism by which second end 11 of material 12 is captured is the same mechanism as shown in FIGS. 3 and 4. In this embodiment, however, first end 13 of material 12 is connected by metallic plate 53 and rivet 50 to the underside of first surface 49 of clasp body 30, rather than to the underside of the clasp body 30 itself. Second end 11 of material 12 passes between metallic plate 53 and second surface 51 of claps body 31. Second surface 51 of clasp body 30 includes an opening 55 through which rivet 50 may be inserted during manufacture.

A third embodiment of clasp 14 as shown in FIGS. 10-13 also allows strap 10 to be adjusted without the need to cut second end 11 of material 12. In this embodiment clasp body 30 has a first surface 49 and two sides 45 to receive woven material 12 in the portion of material 12 between first end 13 and second end 11. Woven material 12 is attached to clasp body 30 by rivet 50 holding metallic plate 53 against the inner surface 22 of material 12. Rivet 50 is connected to fastener 18 which may be connected to a grounding cord 24. A retainer 76 made of anti-static material similar to that found in clasp 30 is attached to first end 13 of material 12. Second end 11 of material 12 passes through retainer 76 and has attached thereto a snap or other fastener 74 formed of anti-static material which may be fastened to snap receptacle 75 placed in material 12 also formed of anti-static material. A plurality of snap receptacles 75 may be placed in material 12 to allow strap 10 to be adjusted to different sizes of wrists.

Figure 5:
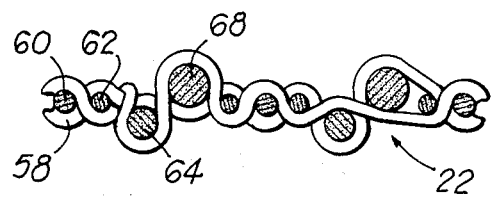
FIG. 5 is an enlarged partial cross sectional view of a portion of a longitudinal cross section of the material of the strap of FIG. 1, taken along line 5—5 of the strap of FIG. 1.
Figure 6:
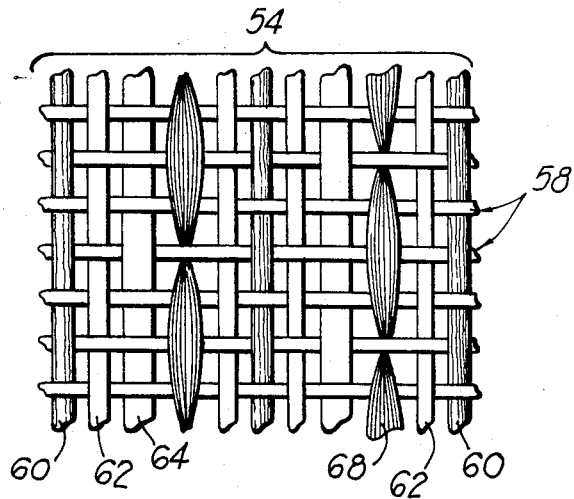
FIG. 6 is an enlarged plan view of a portion of the material of the strap of FIG. 1.

FIGS. 5 and 6 show more fully the structure of woven material 12. FIG. 5 is a cross sectional view taken along line 5-5 of FIG. 1, looking longitudinally into material 12. The yarns shown in cross section are warp yarns 54, while those shown extending around warp yarns 54 are weft yarns 58. Weft yarns 58 are woven about warp yarns 54 and may be made of filament nylon or other synthetic or natural insulative material. In the preferred embodiment, weft yarns 58 are substantially non-stretchable, so that material 12 and strap 10 do not stretch in the lateral direction.

Warp yarns 54 comprise elastic yarns 60, binder yarns 62, conductive yarns 64 and face yarns 68. Elastic yarns 60 and binder yarns 62 form the body of material 12, while conductive yarns 64 appear on inner surface 22 and face yarns 68 appear on outer surface 27. Material 12 is thus conductive on portions of its inner surface 22 and face yarns 68 form designs 26 on its outer surface 27. Material 12 may be woven in extended or partially extended state to allow conductive yarns 64 and face yarns 68 to extend continuously longitudinally through material 12 when stretched, and to form bights or loops when material 12 is relaxed.

Elastic yarns 60 may be formed of stretchable fibers such as spandex fibers or they may be formed of a rubber thread or threads. In the preferred embodiment, elastic yarns 60 are of rubber triple wrapped with polyester. Alternatively, spandex fibers may be used, or spandex fibers may be combined with other natural or synthetic fibers to form elastic yarns 60.

Binder yarns 62 add body to material 12, and serve to insulate electrically conductive yarns 64 from outer surface 27 of material 12. They may be formed of any suitable insulative material and in the preferred embodiment are of spun polyester.

Conductive yarns 64 contact the wearer's skin and conduct static electrical charges to metal plate 53 and rivet 50, which are electrically connected to ground through snap 48 and cords 24. Conductive yarns 64 may be formed of stainless steel fibers such as Bekitex, supplied by the Bekaert Company of Belgium, described in U.S. Pat. No. 3,987,613, which patent is incorporated herein by this reference. Such fibers may be combined with other fibers to form conductive yarns 64, including polyester, nylon or other synthetic or natural fibers. Copper fibers or other metallic or carbon suffused fibers may be used rather than or in combination with stainless steel fibers.

Face yarns 68 serve as insulators and to decorate the outer surface 27 of strap 10. Face yarns 68 are preferably of spun polyester, but may be formed of nylon or other synthetic or natural fibers. Weaving of weft yarns 58 and face yarns 68 may be arranged to form designs 26 on outer surface 27, and face yarns 68 may comprise varying colors to impart either a monochrome or multicolor design 26. Material 12 may be woven on any conventional weaving equipment on which elastic tape is woven, thereby further reducing manufacture expense.

In use, the wearer pulls strap 10 over his hand and onto his wrist, draws material through clasp 14 until strap 10 is comfortably snug about his wrist and then closes gate 28 loosely to grasp second end 11 of material 12. He then marks material 12 parallel to edge 36 of gate 28 and cuts second end 11 of material 12 off at this point. The remaining portion of material 12 is then placed in recess 34 and gate 28 is closed tightly so that edge 36 is biased against lip 38 to hold gate 28 in place. Jam 32 will then prevent material 12 from escaping clasp 14.

In the embodiment shown in FIGS. 7, 8 and 9, second end 11 of material 12 is simply pulled through clasp 14 until strap 10 is comfortably snug about the wearer's wrist. Loop 47 is pulled tight and gate 28 is closed tightly so that edge 36 is biased against lip 38 to hold gate 28 in place. Jam 32 prevents material 12 from escaping clasp 14.

After strap 10 has been placed about the wearer's wrist, grounding cord 24 is connected to snap 48 and electrically connected to ground to remove static charges from the wearer's body. The attractive design 26 and comfort inherent in the woven structure of material 12 lessen the temptation of the wearer to remove it while he is working on microelectronic components or integrated circuits, and the probability of damage to those components or circuits is thereby reduced. The conductive fibers on the inner surface 22 of stretchable woven material 12 cause continuous electrical contact with the wearer's skin so that the probability of stray charges which could damage such components and circuits is reduced.

The foregoing description of this invention is for purposes of explanation and illustration. It will be apparent to those skilled in the relevant art that modifications and changes may be made to the invention as thus described without departing from its scope and spirit.

I claim:

1. A strap for establishing electrical contact with a person's body, comprising:
   (a) a length of woven material for extension in its longitudinal direction circumferentially of the person's wrist, ankle or limb, and comprising:
      (i) a plurality of elastic warp yarns oriented in the longitudinal direction to allow the material to stretch; and
      (ii) a plurality of electrically conductive yarns exposed on the inner surface of the material to contact the person's skin;
   (b) an electrically non-conductive clasp attached to a first end of the material to capture the second end of the material for securing the strap to the person; and
   (c) a fitting attached to the clasp to receive an electrically conductive cord, which fitting is in electrical contact with the conductive yarns.

2. A strap according to claim 1 wherein said woven material further comprises a plurality of longitudinally oriented binder yarns for electrically insulating the conductive yarns from objects that may contact the outer surface of the strap.

3. A strap according to claim 2 wherein said woven material further comprises a plurality of face yarns exposed on the material's outer surface to impart an attractive appearance to the outer surface of the strap.

4. A strap according to claim 1 wherein said woven material futher comprises a plurality of weft yarns of nylon filament.

5. A strap according to claim 1 wherein said electrically conductive yarns comprise stainless steel fibers.

6. A strap according to claim 1 wherein said electrically conductive yarns comprise carbon-suffused synthetic material.

7. A strap according to claim 1 wherein each of said elastic yarns comprises:
   (a) at least one rubber strand; and
   (b) at least one strand of polyester fibers wrapped about the rubber strand.

8. A strap according to claim 3 wherein said binder yarns and said facing yarns comprise spun polyester.

9. A strap according to claim 1 wherein said clasp adjustably captures said second end of said woven material.

10. A strap according to claim 1 further comprising a metal plate in electrical contact with said electrically conductive yarns and electrically and mechanically connected to said fitting, for forming an electrically conductive plate surface adjacent to said clasp.

11. A strap according to claim 10 wherein said clasp is of antistatic material and comprises:
    (a) A body having:
       (i) a first surface for receiving said fitting;
       (ii) a second surface for receiving said first end of said woven material; and
       (iii) an opening communicating between the first and second sufaces for connecting the fitting, the body, the woven material and said plate; and
       (iv) a recess for holding said second end of the woven material; and
    (b) a gate pivotally connected to the body and having a jam for clamping the second end of material into place when the gate is closed.

12. Woven elastic electrically conductive material comprising:
    (a) a plurality of elastic warp yarns to allow the material to stretch;
    (b) a plurality of electrically conductive warp yarns exposed on a first side of the material; and
    (c) a plurality of weft yarns.

13. Woven elastic electrically conductive material according to claim 12 further comprising:
    (a) a plurality of binder warp yarns for electrically insulating said conductive yarns from objects that may contact the second side of the material.

14. Woven elastic electrically conductive material according to claim 12 further comprising a plurality of facing yarns on the second side of the material to impart an attractive appearance to the material.

15. Woven elastic electrically conductive material comprising:
    (a) a plurality of elastic warp yarns to allow the material to stretch, each comprising:
       (i) at least one rubber strand; and
       (ii) at least one strand of polyester fibers wrapped about the rubber strand;
    (b) a plurality of electrically conductive warp yarns exposed on a first side of the material;
    (c) a plurality of binder warp yarns for electrically insulating the conductive yarns from objects that may contact the second surface of the material;
    (d) a plurality of facing warp yarns exposed in the second side of the material for imparting an attractive appearance to the material; and
    (e) a plurality of weft yarns.

16. Woven elastic electrically conductive material according to claim 15 wherein said electrically conductive warp yarns comprise stainless steel fibers.

17. Woven elastic electrically conductive material according to claim 15 wherein said electrically conductive warp yarns comprise carbon-suffused synthetic fibers.

* * * * *